(12) United States Patent
Molt et al.

(10) Patent No.: US 7,803,948 B2
(45) Date of Patent: Sep. 28, 2010

(54) METHOD FOR THE ISOMERISATION OF TRANSITION METAL COMPLEXES CONTAINING CYCLOMETALLATED, CARBENE LIGANDS

(75) Inventors: Oliver Molt, Hirschberg (DE); Klaus Kahle, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 173 days.

(21) Appl. No.: 11/916,455

(22) PCT Filed: Jun. 13, 2006

(86) PCT No.: PCT/EP2006/063165

§ 371 (c)(1),
(2), (4) Date: Dec. 4, 2007

(87) PCT Pub. No.: WO2006/134113

PCT Pub. Date: Dec. 21, 2006

(65) Prior Publication Data

US 2008/0200686 A1    Aug. 21, 2008

(30) Foreign Application Priority Data

Jun. 14, 2005    (DE) .................. 10 2005 027 548

(51) Int. Cl.
*C07F 15/00*    (2006.01)

(52) U.S. Cl. ...................................... 548/103
(58) Field of Classification Search .............. 548/103
See application file for complete search history.

(56) References Cited

U.S. PATENT DOCUMENTS

2002/0121638 A1* 9/2002 Grushin et al. .............. 257/40

FOREIGN PATENT DOCUMENTS

DE    10 2004 057 072    6/2006
WO    2005/019373    3/2005

OTHER PUBLICATIONS

Holmes et al., 2005, CAS: 144:201132.*
Tamayo, Arnold B. et al., "Synthesis and Characterization of Facial and Meridional Tris-cyclometalated Iridium (III) complexes", Journal of American Chemical Society, vol. 125, pp. 7377-7387, 2003.

* cited by examiner

*Primary Examiner*—Rei-tsang Shiao
(74) *Attorney, Agent, or Firm*—Oblon, Spivak, McClelland, Maier & Neustadt, L.L.P.

(57) ABSTRACT

A process for converting a compound $C^1$ of the formula I in a mer isomer form

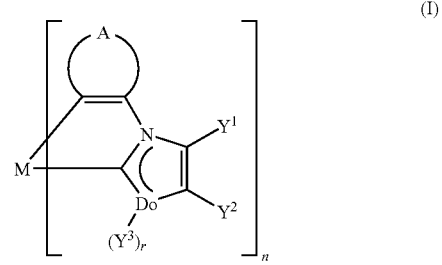

into an isomeric compound $C^2$ of the formula I in a fac isomer form.

13 Claims, No Drawings

METHOD FOR THE ISOMERISATION OF TRANSITION METAL COMPLEXES CONTAINING CYCLOMETALLATED, CARBENE LIGANDS

The present invention relates to a process for converting an isomerically pure compound $C^1$ of the formula I

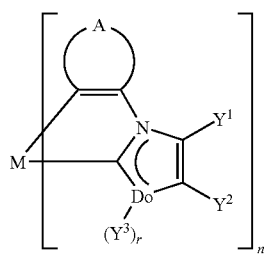

or a mixture $M^1$ comprising $C^1$ into an isomeric compound $C^2$ of the formula I which is different from $C^1$ or a mixture $M^2$ comprising $C^2$, where the variables have the following meanings:

n is 2 or 3;

M is Pd or Pt, in each case in the formal oxidation state +II, when n is 2;

and is Ru, Os, Co, Rh or Ir, in each case in the formal oxidation state +III, when n is 3;

Do is a donor atom selected from the group consisting of N, O, S and P;

r is 1 when Do is N or P, and is 0 when Do is O or S;

$Y^1$, $Y^2$ are each, independently of one another, hydrogen, alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ or NO, or $Y^1$ and $Y^2$ together with the carbon atoms to which they are bound form a six-membered aromatic ring which may comprise one or two nitrogen atoms and may optionally be fused with a further, optionally fused and optionally heteroatom-comprising ring;

$Y^3$ is alkyl, alkenyl, alkynyl, aryl or heteroaryl;

A is a bridge having three or four atoms of which one or two atoms may be heteroatoms and the remaining atoms are carbon atoms, so that the group

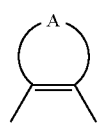

forms a five- or six-membered heteroaromatic ring or benzene ring which may optionally be substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO and may optionally be fused with a further, optionally heteroatom-comprising ring which may likewise be fused and substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO;

which comprises allowing a Brönsted acid or a mixture of Brönsted acids to act on $C^1$ or $M^1$ in the presence of a solvent or solvent mixture at a temperature of from 0° C. to the boiling point of the solvent or the solvent mixture, with the proviso that a) the formation of $C^2$ from $C^1$ occurs under the conditions of the process
and
b) when both $M^1$ and $M^2$ are mixtures comprising $C^1$ and $C^2$, the respective isomer ratios of $C^1$ and $C^2$ in the mixtures $M^1$ and $M^2$ are different from one another.

Organic light-emitting diodes (OLEDs) exploit the ability of particular materials to emit light when they are excited by means of an electric current. The numerous materials which have been proposed as emitters for OLEDs include cyclometallated transition metal complexes comprising carbene ligands as described in WO 05/019373 A2 and the earlier German patent application DE 10 2004 057072.8. The synthesis of the homoleptic complexes disclosed in these documents, in which the metal centers are coordinated only by cyclometallated carbene ligands, usually gives mixtures of cis/trans or fac/mer isomers. With regard to their properties as emitters in OLEDs, these isomers generally display differing behavior, which is why the isolation of the desired isomer is usually carried out by means of appropriate methods in a further step. Particularly in the case of syntheses in which the desired isomer is formed as minor component, achieving an increase in its proportion by means of suitable procedures is not only desirable but indispensable with a view to efficient and inexpensive preparation.

It was thus an object of the present invention to provide a process which makes it possible to increase the proportion of the desired isomer of the formula I shown at the outset in a simple manner starting from its other isomer or from an isomer mixture in which this desired isomer is present as minor component.

This object is achieved by the process described at the outset.

A critical aspect of the process of the invention is that the desired isomer $C^2$ is formed from the isomer $C^1$ under the conditions of the process. For example, the formation of $C^2$ from the pure compound $C^1$ can occur quantitatively or a mixture of the isomers $C^2$ and $C^1$ is obtained. This also implies that a mixture $M^1$ comprising $C^1$ is converted under the conditions of the process into a mixture $M^2$ comprising a higher proportion of the isomer $C^2$ than the mixture $M^1$. Here, $M^1$ can comprise $C^1$ together with $C^2$, but does not have to. Furthermore, mixture $M^1$ can comprise $C^1$ together with further components such as by-products resulting from the method of preparation.

If the isomerically pure compound $C^1$ is converted by means of the process of the invention into a mixture $M^2$ comprising the desired isomeric compound $C^2$ together with $C^1$, it is generally possible to separate off the latter compound, for example by chromatography, and to subject it once again to the process of the invention. In cases in which the isomerization according to the invention of $C^1$ to $C^2$ occurs quantitatively, this iterative procedure becomes superfluous.

The process of the invention is preferably employed for the isomerization of compounds of the formula I in which the variables have the following meanings:

n is 2 or 3;

M is Pd or Pt, in each case in the formal oxidation state +II, when n is 2;

and is Rh or Ir, in each case in the formal oxidation state +III, when n is 3;

Do is a donor atom N;

r is 1;

$Y^1, Y^2$ are each, independently of one another, hydrogen or alkyl or $Y^1$ and $Y^2$ together with the carbon atoms to which they are bound form a six-membered aromatic ring which may comprise one or two nitrogen atoms;

$Y^3$ is alkyl, aryl or heteroaryl;

A is a bridge having three or four atoms of which one or two atoms may be heteroatoms and the remaining atoms are carbon atoms, so that the group

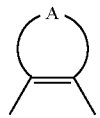

forms a five- or six-membered heteroaromatic ring or benzene ring which may optionally be substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO.

The process of the invention is particularly preferably employed for the isomerization of compounds of the formula I in which the variables have the following meanings:

n is 2 or 3;

M is Pd or Pt, in each case in the formal oxidation state +II, when n is 2;

and is Rh or Ir, in each case in the formal oxidation state +III, when n is 3;

Do is a donor atom N;

r is 1;

$Y^1, Y^2$ are each, independently of one another, hydrogen or alkyl or $Y^1$ and $Y^2$ together with the carbon atoms to which they are bound form a benzene ring;

$Y^3$ is alkyl or aryl;

A is a bridge having four atoms of which one atom may be a heteroatom and the remaining atoms are carbon atoms, so that the group

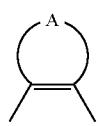

forms a six-membered heteroaromatic ring or benzene ring which may optionally be substituted by substituents selected from the group consisting of alkyl, alkyloxy, aryl, aryloxy, alkylcarbonyl, arylcarbonyl, alkoxycarbonyl, aryloxycarbonyl, halogen and CN.

The process of the invention is very particularly preferably employed for the isomerization of compounds of the formula I in which the variables have the following meanings:

n is 2 or 3;

M is Pd or Pt, in each case in the formal oxidation state +II, when n is 2;

and is Rh or Ir, in each case in the formal oxidation state +III, when n is 3;

Do is a donor atom N;

r is 1;

$Y^1, Y^2$ are each hydrogen or $Y^1$ and $Y^2$ together with the carbon atoms to which they are bound form a benzene ring;

$Y^3$ is alkyl or aryl;

A is a bridge having four atoms of which one atom may be a nitrogen atom and the remaining atoms are carbon atoms, so that the group

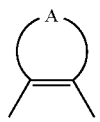

forms a pyridine or benzene ring which may optionally be substituted by substituents selected from the group consisting of alkyl, alkyloxy, aryl, aryloxy, alkylcarbonyl, arylcarbonyl, alkoxycarbonyl, aryloxycarbonyl, halogen and CN.

For the purposes of the present patent application, the terms alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl and halogen have the following meanings:

The term alkyl refers to a radical having from 1 to 20 carbon atoms, preferably from 1 to 10 carbon atoms, particularly preferably from 1 to 8 carbon atoms. The alkyl radical can be branched or unbranched and may optionally be interrupted by one or more heteroatoms, preferably Si, N, O or S, particularly preferably N, O or S. Furthermore, the alkyl radical may be substituted by one or more substituents mentioned under the definition of aryl. It is likewise possible for the alkyl radical to bear one or more aryl groups. Here, all of the abovementioned aryl groups are suitable. Alkyl is particularly preferably selected from the group consisting of methyl, ethyl, n-propyl, isopropyl and tert-butyl.

The alkyloxy, alkylthio and alkylcarbonyl radicals are formally obtained by bonding of the corresponding abovementioned alkyl radicals to an oxygen atom, a sulfur atom or a carbonyl group, and the alkoxycarbonyl and alkyloxysulfonyl radicals are, once again formally, obtained by bonding of the corresponding alkyloxy radicals to a carbonyl group or a sulfonyl group.

The term alkenyl refers to a radical which corresponds to the abovementioned alkyl having at least two carbon atoms, with the difference that at least one C—C single bond of the alkyl is, if possible, replaced by a C—C double bond. The alkenyl radical preferably has one or two double bonds.

The term alkynyl correspondingly refers to a radical which corresponds to the abovementioned alkyl having at least two carbon atoms, with the difference that at least one C—C single bond of the alkyl is, if possible, replaced by a C—C triple bond. The alkynyl radical preferably has one or two triple bonds.

The term aryl refers to a radical which has a skeleton of from 6 to 30 carbon atoms, preferably from 6 to 18 carbon atoms, and is made up of an aromatic ring or a plurality of fused aromatic rings. Suitable skeletons are, for example, phenyl, naphthyl, anthracenyl or phenanthrenyl. This skeleton can be unsubstituted (i.e. all carbon atoms which are substitutable bear hydrogen atoms) or be substituted on one, more than one or all substitutable positions of the skeleton. Suitable substituents are, for example, alkyl radicals, preferably alkyl radicals having from 1 to 8 carbon atoms, particularly preferably methyl, ethyl or i-propyl, aryl radicals, preferably $C_6$-aryl radicals, which may once again be substituted or unsubstituted, heteroaryl radicals, preferably heteroaryl radicals comprising at least one nitrogen atom, particularly preferably pyridyl radicals, alkenyl radicals, preferably alkenyl radicals having one double bond, particularly preferably alkenyl radicals having one double bond and from 1 to 8 carbon atoms, or groups having a donor or acceptor action. For the purposes of the present invention, groups having a donor action are groups which have a +I and/or +M effect, and groups having an acceptor action are groups which have a –I and/or –M effect. Suitable groups having a donor or acceptor action are halogen radicals, preferably F, Cl, Br, particularly preferably F, alkoxy radicals, aryloxy radicals, carbonyl radicals, ester radicals, amine radicals, e.g. alkylamine, dialkylamine, arylamine, diarylamine radicals or diarylamine radicals having bridged aryl radicals, e.g. 1-carbazolyl, amide radicals, $CH_2F$ groups, $CHF_2$ groups, $CF_3$ groups, CN groups, thio groups, SCN, nitro and NO groups. If the aryl radicals are substituted they very particularly preferably bear substituents selected from the group consisting of methyl, F, Cl, aryloxy and alkoxy. Aryl is preferably a $C_6$-$C_{18}$-aryl radical, particularly preferably a $C_6$-aryl radical which may optionally be substituted by at least one of the abovementioned substituents. The $C_6$-$C_{18}$-aryl radical, preferably $C_6$-aryl radical, preferably has none, one or two of the abovementioned substituents, with a single substituent being arranged in the ortho, meta or para position relative to the further point of linkage of the aryl radical, and two substituents each being able to be arranged in the meta position or ortho position relative to the further point of linkage of the aryl radical or one radical being located in the ortho position and one radical being located in the meta position or one radical being located in the ortho or meta position and the further radical being located in the para position.

The aryloxy, arylthio and arylcarbonyl radicals are formally obtained by bonding of the corresponding abovementioned aryl radicals to an oxygen atom, a sulfur atom or a carbonyl group, and the aryloxycarbonyl and aryloxysulfonyl radicals are, once again formally, obtained by bonding of the corresponding aryloxy radicals to a carbonyl group or a sulfonyl group.

The term heteroaryl refers to radicals which differ from the abovementioned aryl radicals by at least one carbon atom in the aryl skeleton being replaced by a heteroatom. Preferred heteroatoms are N, O and S. Very particular preference is given to one or two carbon atoms of the aryl skeleton being replaced by heteroatoms. The skeleton is particularly preferably selected from systems such as pyridine and five-membered heteroaromatics such as pyrrole or furan. The skeleton can be substituted in one, more than one or all substitutable positions of the skeleton. Suitable substituents are the same as those which have been mentioned above under the definition of aryl.

The variables $Y^1$ and $Y^2$ are each, independently of one another, hydrogen, alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ or NO. Preference is given to $Y^1$ and $Y^2$ each being, independently of one another, hydrogen or alkyl, with the latter being, in particular, $C_1$-$C_4$-alkyl such as methyl, ethyl, n-propyl, isopropyl or tert-butyl. $Y^1$ and $Y^2$ are particularly preferably each hydrogen.

Furthermore, it is possible for $Y^1$ and $Y^2$ together with the carbon atoms to which they are bound to form a six-membered aromatic ring which may comprise one or two nitrogen atoms. This can be fused with a further, optionally fused and optionally heteroatom-comprising ring. Here, the heteroatoms can be part of the ring or be bound to the ring ("in exo positions"). Preference is given to $Y^1$ and $Y^2$ together with the carbon atoms to which they are bound forming a six-membered aromatic ring which may comprise one or two nitrogen atoms. Particular preference is given to $Y^1$ and $Y^2$ together with the carbon atoms to which they are bound forming a benzene ring.

Corresponding fused substructures of the carbene ligands are shown by way of example below:

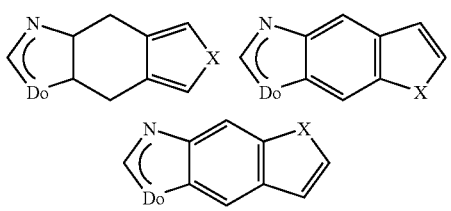

X = $CR_2$, C(O), O, S, NR; R = hydrogen, alkyl, aryl

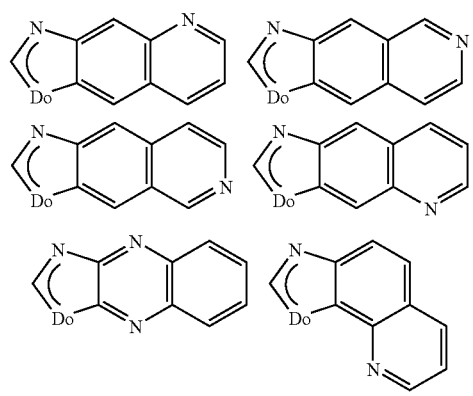

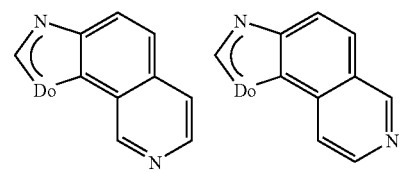

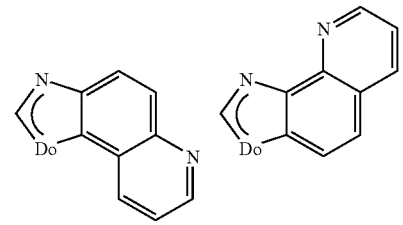

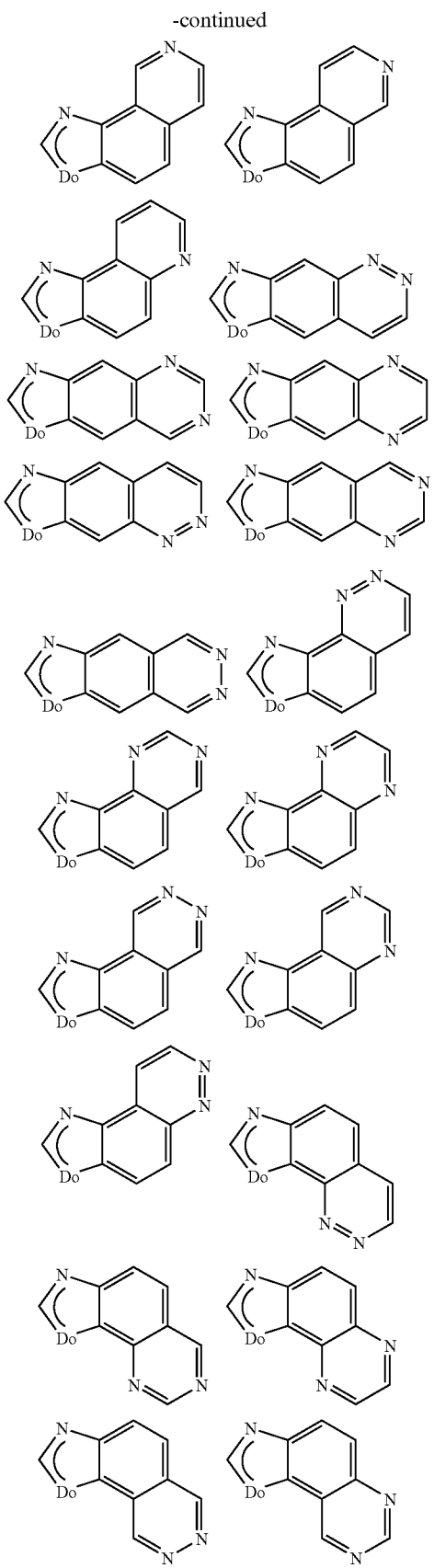

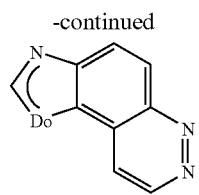

Furthermore, more highly fused substructures derived from the substructures shown above, e.g. by benzo-fusion, are also possible.

Further examples of more highly fused substructures of the carbene ligands are:

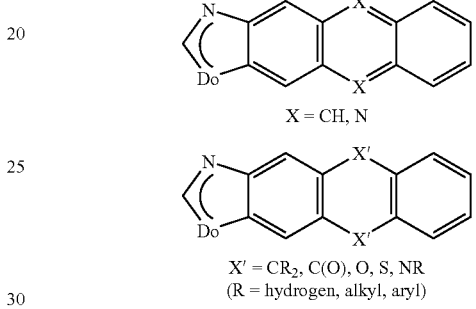

Preferred and particularly preferred substructures for the carbene ligands are:

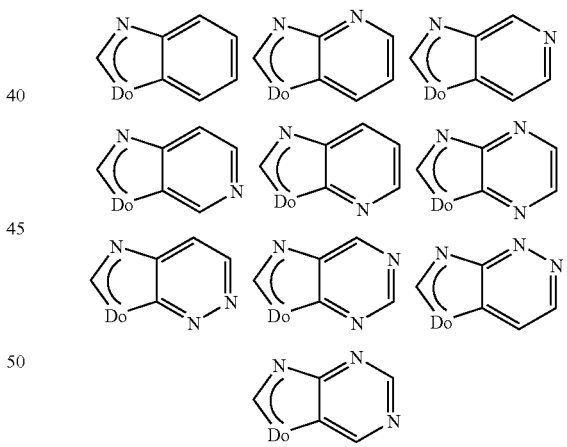

where Do is N, O, S or P, in particular N.

If Do is N or P, in particular N, the variable $Y^3$ in formula I is alkyl, alkenyl, alkynyl, aryl or heteroaryl, preferably alkyl, aryl or heteroaryl, particularly preferably alkyl or aryl. As alkyl, particular mention may be made of $C_1$-$C_4$-alkyl, such as methyl, ethyl, n-propyl, isopropyl or tert-butyl, and an aryl group deserving of particular mention is phenyl.

The variable A in formula I is a bridge having three or four atoms of which one or two atoms can be heteroatoms and the remaining atoms are carbon atoms, so that the group

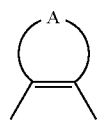

(hereinafter also referred to as "G") forms a five- or six-membered heteroaromatic ring or a benzene ring. Possible heteroatoms are, in particular, O, N and S. The group G may be substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO. If the substituents mentioned comprise heteroatoms, they are usually bound to the group G via carbon atoms of the group G. However, bonding can also take place via suitable heteroatoms of the group G.

Suitable five-membered heteroaromatic rings as group G are shown below:

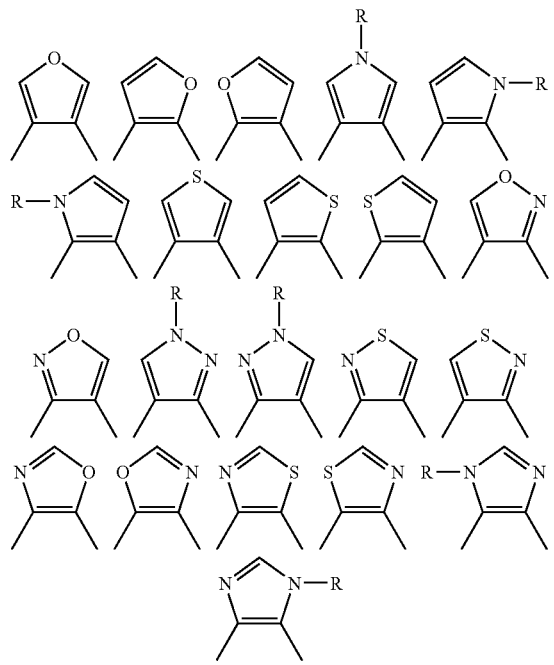

where R is, in particular, hydrogen, alkyl, alkenyl, alkynyl, aryl or heteroaryl, as defined above, with the bonding of the ring nitrogen in the case of R=heteroaryl occurring via a carbon atom or, if appropriate, via a suitable heteroatom of the heteroaryl.

Suitable six-membered heteroaromatic rings as group G are:

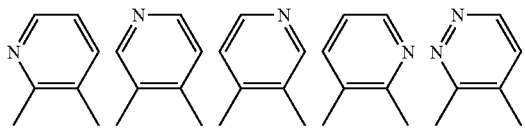

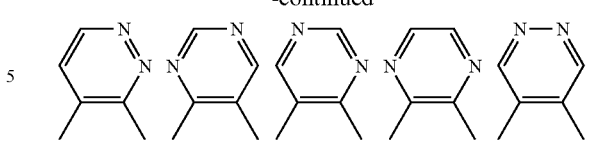

Furthermore, the group G can also be fused with a further, optionally heteroatom-comprising ring, with the latter ring in turn being able to be fused and substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO.

Examples of such more highly fused groups G are:

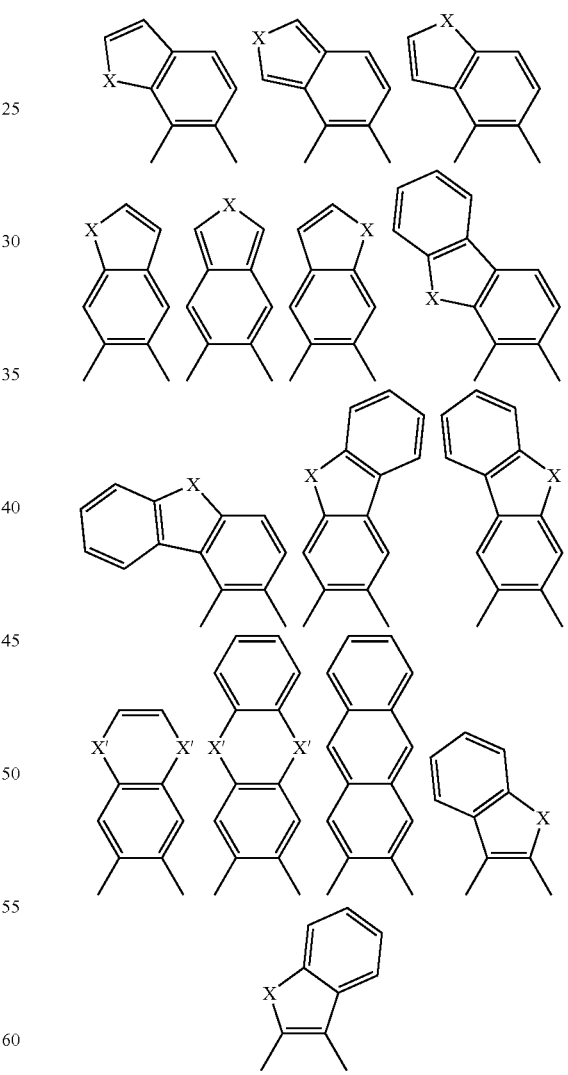

where X is O, S or NR, where R is hydrogen, alkyl or aryl, and the two radicals X' are each, independently of one another, a carbonyl group, $CR_2$ group, O, S or NR, where R is hydrogen, alkyl or aryl.

Preferred fused groups G are:

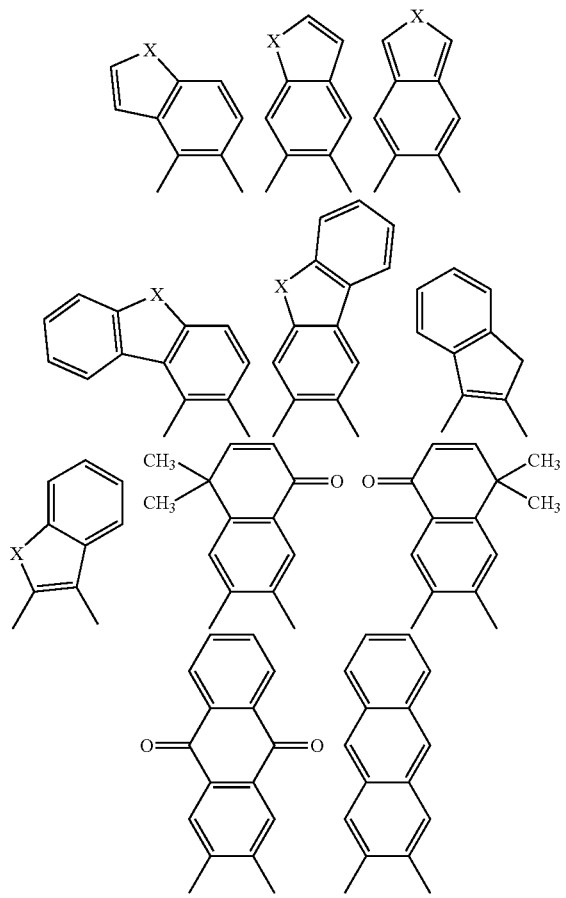

where X is O, S or NR, where R is hydrogen, alkyl or aryl, preferably hydrogen or alkyl.

A preferably forms a bridge having three or four atoms of which one or two atoms may be heteroatoms and the remaining atoms are carbon atoms, so that the group G forms a five- or six-membered heteroaromatic ring or benzene ring which may optionally be substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO.

A particularly preferably forms a bridge having four atoms of which one atom can be a heteroatom and the remaining atoms are carbon atoms, so that the group G forms a six-membered heteroaromatic ring or benzene ring which may optionally be substituted by substituents selected from the group consisting of alkyl, alkyloxy, aryl, aryloxy, alkylcarbonyl, arylcarbonyl, alkyloxycarbonyl, aryloxycarbonyl, halogen and CN.

A very particularly preferably forms a bridge having four atoms of which one atom can be a nitrogen atom and the remaining atoms are carbon atoms, so that the group G forms a pyridine or benzene ring which may optionally be substituted by substituents selected from the group consisting of alkyl, alkyloxy, aryl, aryloxy, alkylcarbonyl, arylcarbonyl, alkyloxycarbonyl, aryloxycarbonyl, halogen and CN.

In particular, the group G can be:

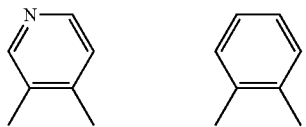

where the group G may be substituted in accordance with the above-described preferences. If the substituents mentioned comprise heteroatoms, they are usually bound to the group G via carbon atoms of the group G, but can also be bound via suitable heteroatoms of the group G.

As substituted groups G, particular mention may be made of the following:

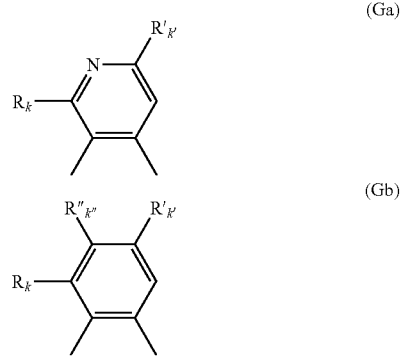

where R" is CN, CHO, alkylcarbonyl, arylcarbonyl, carboxyl, alkyloxycarbonyl, aryloxycarbonyl, hydroxysulfonyl, alkyloxysulfonyl, aryloxysulfonyl, $NO_2$ or NO, k" is 0 or 1, R and R' are each, independently of one another, alkyl or halogen, in particular fluorine, and k and k' are each 0 or 1, with the proviso that in the group (Ga) the sum of k and k' is 1 or 2 and in group (Gb) the sum of k and k' is 1 or 2 when k" is 0 and the sum of k and k" is 0, 1 or 2 when k" is 1. When k" is 0, the sum of k and k' is preferably 2; when k" is 1, the sum of k and k" is preferably 0 or 2. A value of 0 for k, k' or k" means that none of the abovementioned substituents R, R' or R" is present in the corresponding position of the ring and a hydrogen atom is therefore located in this position. If k and k' are each 1, the substituents are preferably identical.

Possible alkyl radicals R and R' are, in particular, methyl, ethyl, n-propyl, isopropyl and tert-butyl. Alkyl or aryl present in the radicals corresponding to the definition of R' is, in particular, methyl, ethyl, n-propyl, isopropyl or tert-butyl, or phenyl, naphthyl, anthracenyl or phenanthrenyl which may each be substituted by substituents selected from the group consisting of methyl, F, Cl, phenoxy, methoxy, ethoxy, n-propoxy, isopropoxy and tert-butoxy, with optionally substituted phenyl being preferred.

Examples of such substituted groups G are:

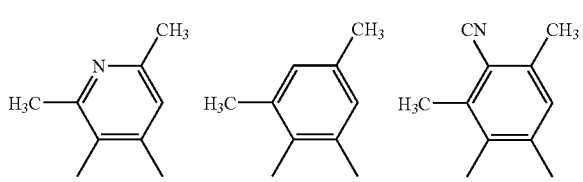

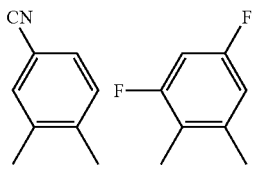
Compounds C¹ which can be isomerized by means of the process of the invention are, for example,
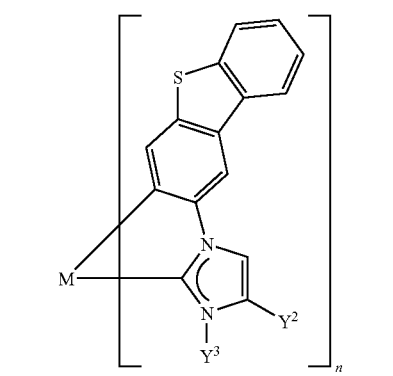
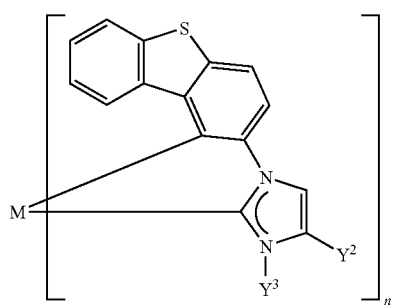
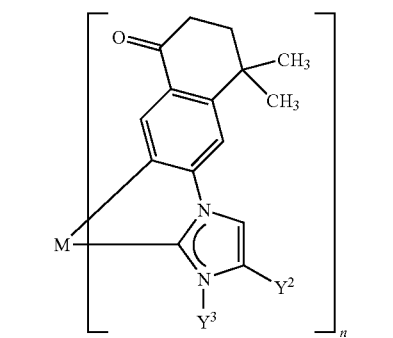
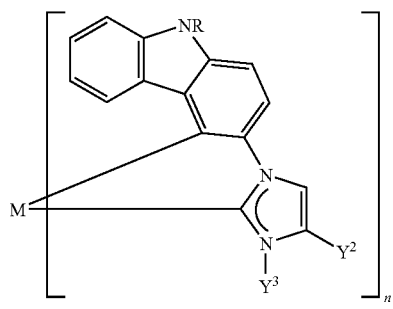
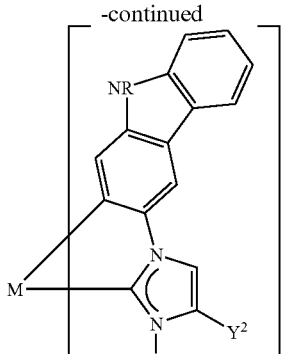
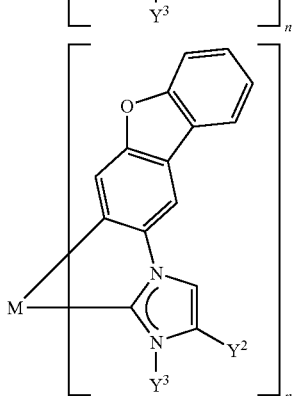
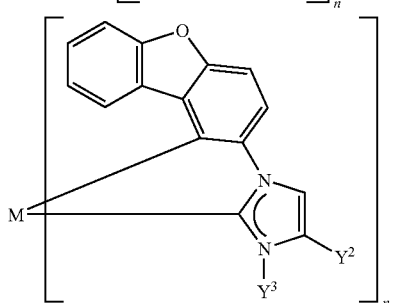
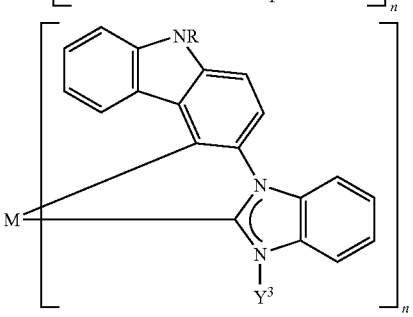
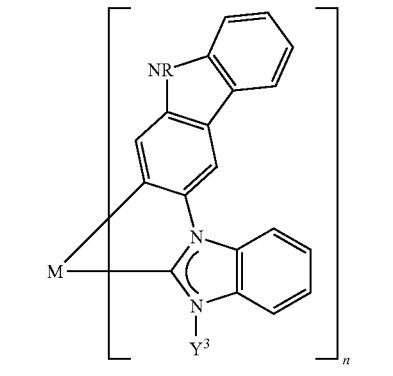

-continued
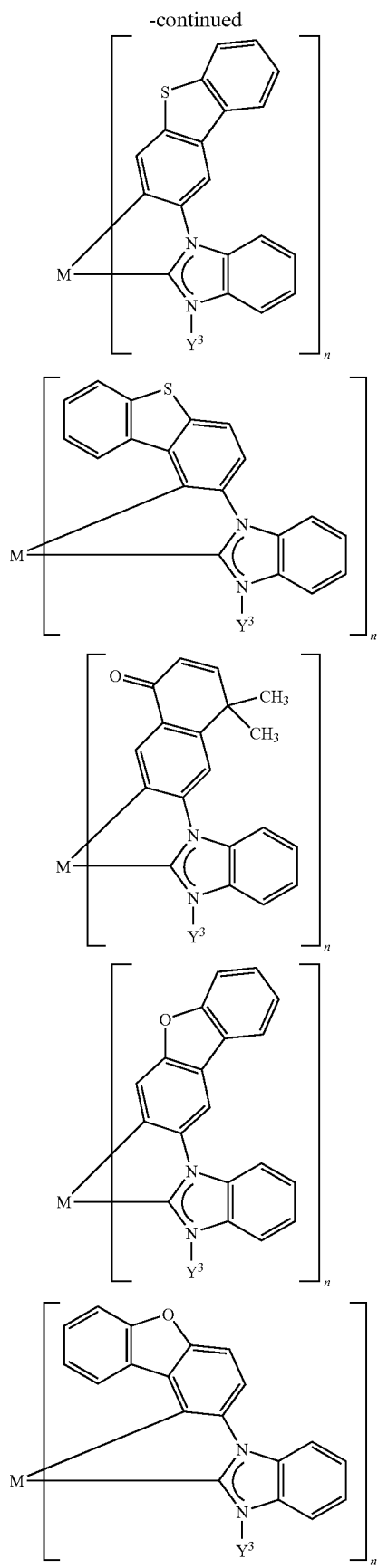
-continued
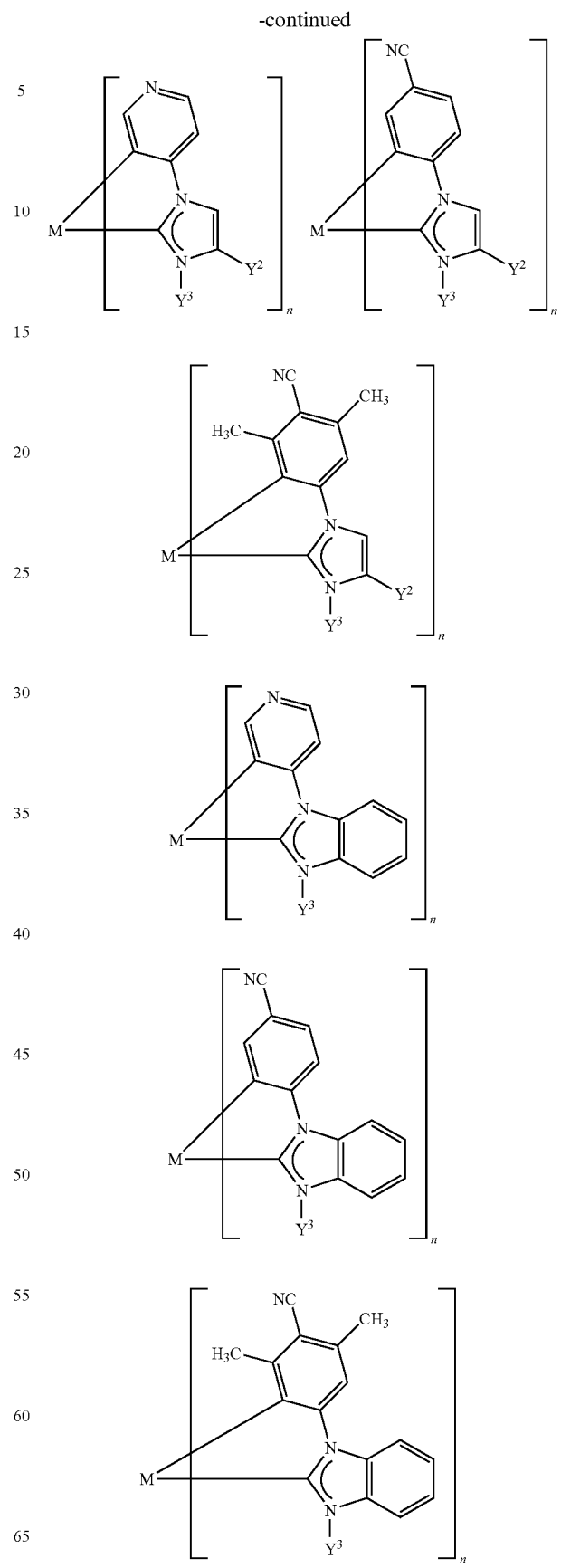

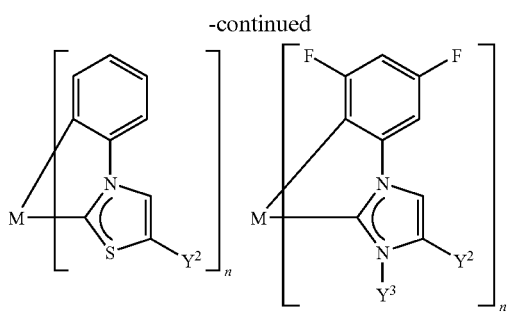
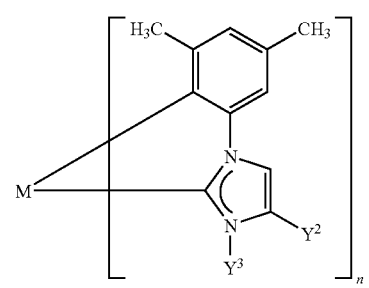
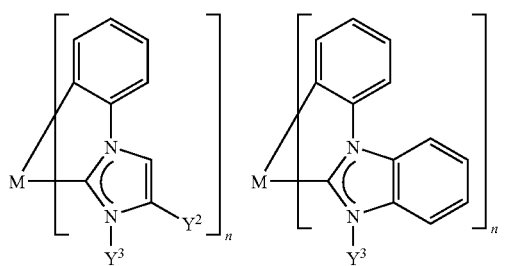
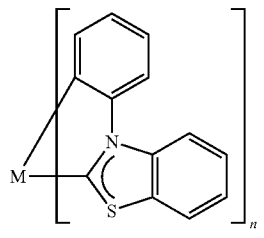
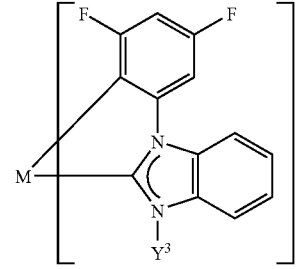
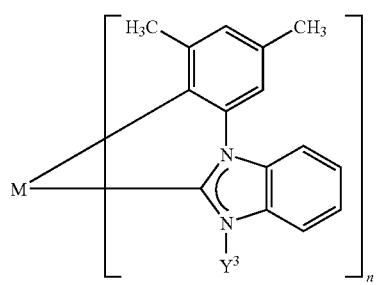
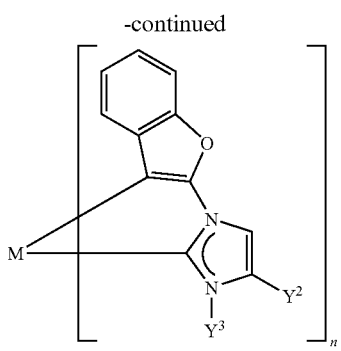
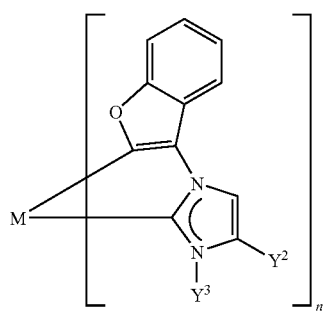
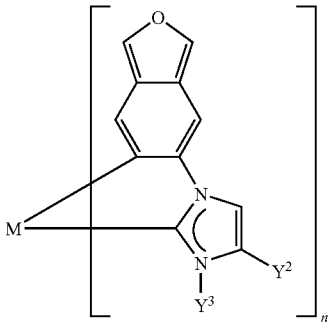
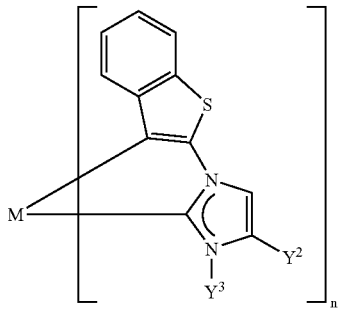
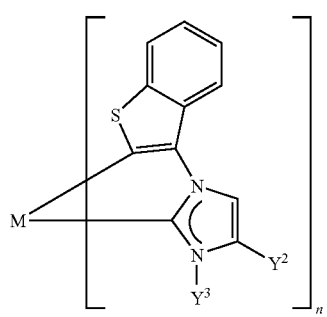

-continued
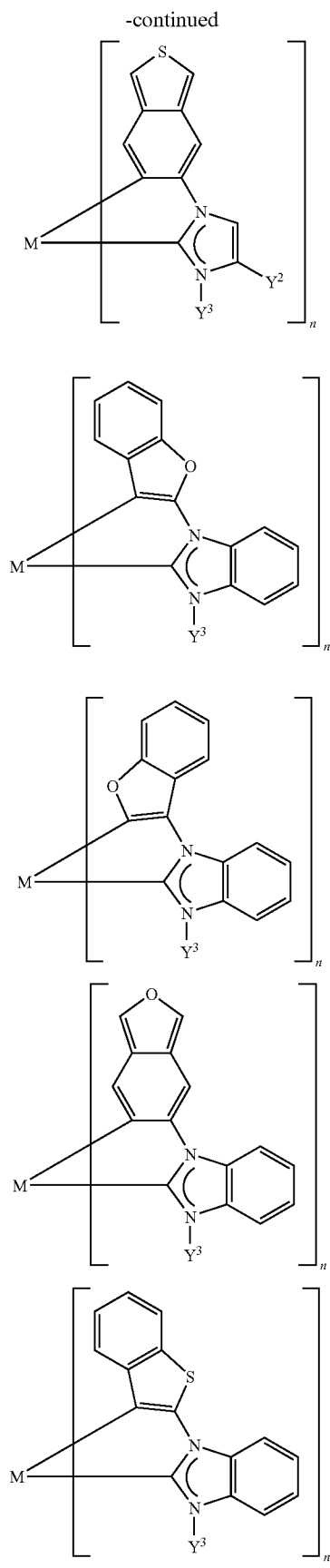
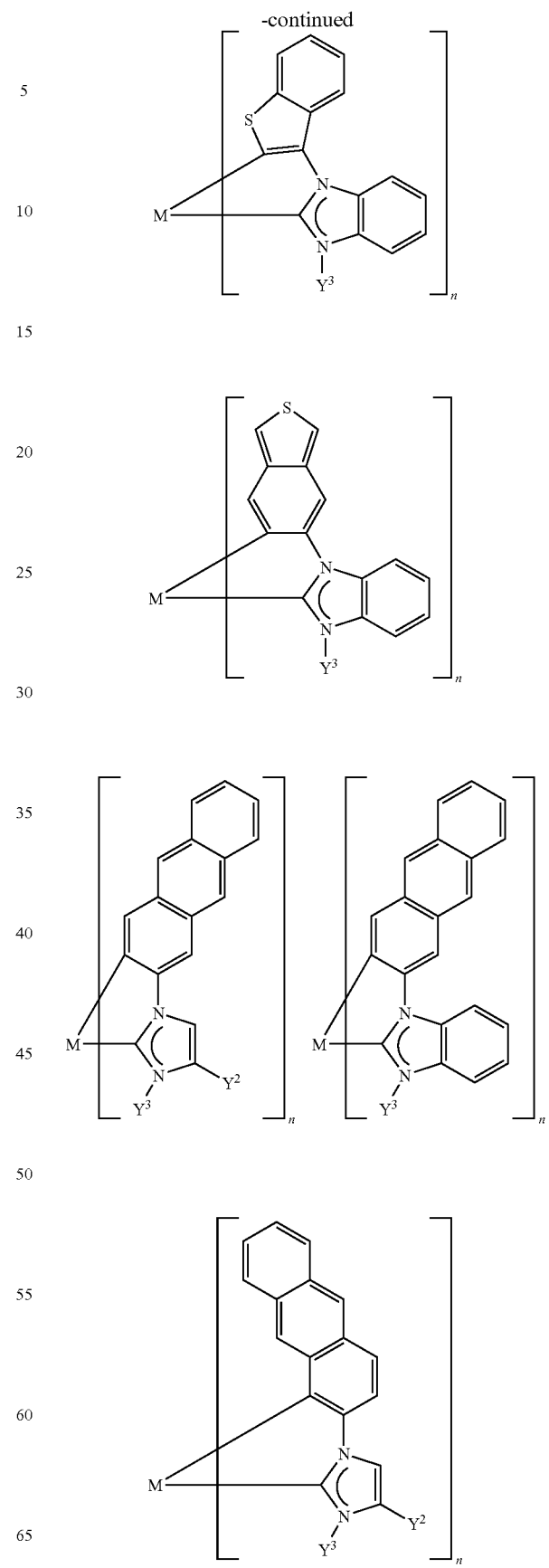

-continued

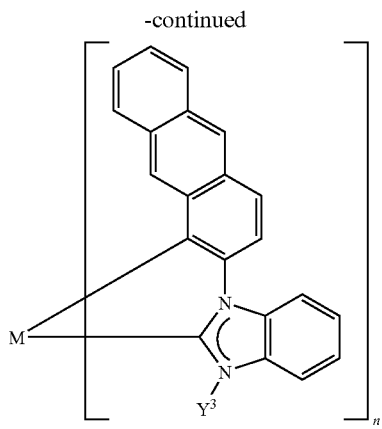

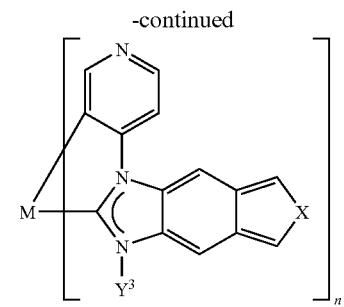

where M is Ru(III), Os(III), Co(III), Rh(II), Ir(III), Pd(II) or Pt(II), n is 3 in the case of Ru(III), Os(III), Co(III), Rh(III) and Ir(III), and is 2 in the case of Pd(II) and Pt(II), and the variables $Y^2$ and $Y^3$ correspond to the general definitions and their preferences given above. Accordingly, the variable $Y^3$ is alkyl, alkenyl, alkynyl, aryl or heteroaryl, preferably alkyl, aryl or heteroaryl, particularly preferably alkyl or aryl. As alkyl, particular mention may be made of $C_1$-$C_4$-alkyl such as methyl, ethyl, n-propyl, isopropyl or tert-butyl, and an aryl radical which deserves particular mention is phenyl. The variable $Y^2$ is hydrogen, alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ or NO, preferably hydrogen or alkyl, particularly preferably hydrogen.

Further compounds $C^1$ of the formula I which can be isomerized by means of the process of the invention are, for example,

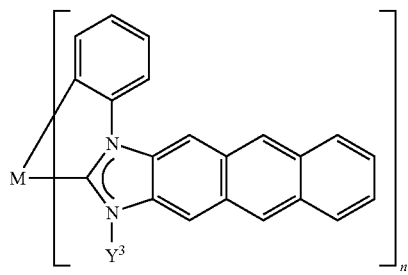

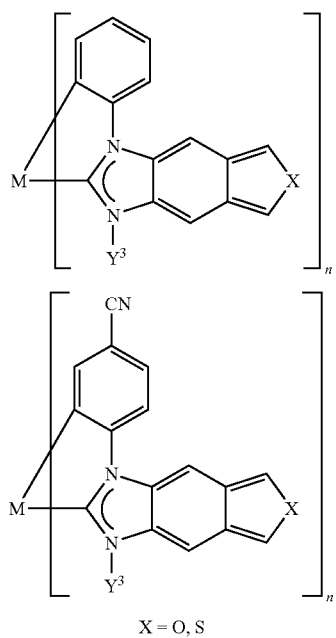

X = O, S

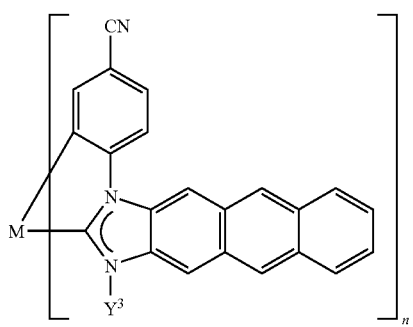

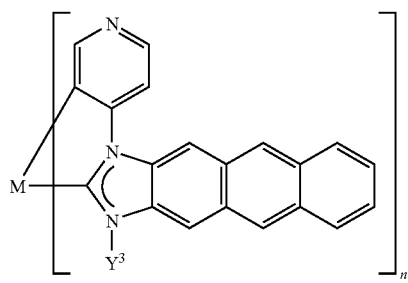

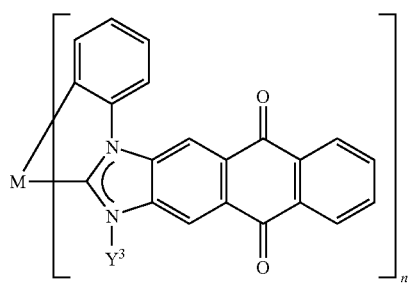

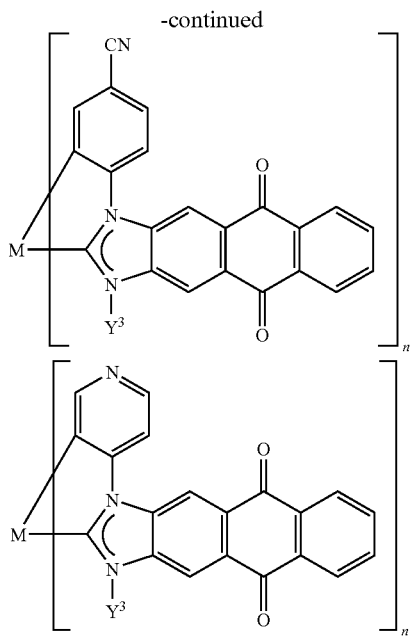

where M is Ru(III), Os(III), Co(III), Rh(III), Ir(III), Pd(II) or Pt(II), n is 3 in the case of Ru(III), Os(III), Co(III), Rh(III) and Ir(III), and is 2 in the case of Pd(II) and Pt(II), and the variable $Y^3$ corresponds to the general definition and its preferences given above. The variable $Y^3$ is accordingly alkyl, alkenyl, alkynyl, aryl or heteroaryl, preferably alkyl, aryl or heteroaryl, particularly preferably alkyl or aryl. As alkyl, particular mention may be made of $C_1$-$C_4$-alkyl such as methyl, ethyl, n-propyl, isopropyl or tert-butyl, and an aryl radical which deserves particular mention is phenyl.

The process of the invention is preferably carried out using a solvent or solvent mixture comprising one or more compounds selected from the group consisting of water, $C_1$-$C_4$-alkanols, symmetrical and unsymmetrical di($C_1$-$C_4$)-alkyl ethers, symmetrical and unsymmetrical di($C_1$-$C_4$)-alkyl ketones, partially halogenated $C_1$-$C_4$-alkanes, perhalogenated $C_1$-$C_4$-alkanes, partially halogenated $C_2$-$C_4$-alkenes, perhalogenated $C_2$-$C_4$-alkenes, five- and six-membered saturated cyclic ethers having one oxygen atom, six-membered saturated cyclic ethers having two nonadjacent oxygen atoms, N—$C_1$-$C_4$-alkylformamides, N,N-di($C_1$-$C_4$-alkyl)formamides, N—$C_1$-$C_4$-alkylacetamides, N,N-di($C_1$-$C_4$-alkyl)acetamides, five-, six- and seven-membered saturated lactones, five-, six- and seven-membered saturated lactams, $C_1$-$C_4$-alkyl $C_1$-$C_4$-alkanoates, symmetrical and unsymmetrical di($C_1$-$C_4$)-alkyl sulfoxides, nitrites of $C_2$-$C_4$-carboxylic acids, nitriles of monocyclic aromatic carboxylic acids, monocyclic aromatics and monocyclic heteroaromatics.

$C_1$-$C_4$-Alkanols are, for example, methanol, ethanol, propanol, isopropanol, butanol, sec-butanol and isobutanol.

Symmetrical and unsymmetrical di($C_1$-$C_4$)-alkyl ethers are, in particular, dimethyl ether and diethyl ether.

Symmetrical and unsymmetrical di($C_1$-$C_4$)-alkyl ketones are, in particular, acetone, methyl ethyl ketone and methyl tert-butyl ketone.

Partially halogenated $C_1$-$C_4$-alkanes are, in particular, methylene chloride, chloroform, 1,1- and 1,2-dichloroethane, 1,1,1- and 1,1,2-trichloroethane and also 1,2- and 1,3-dichloropropane.

Perhalogenated $C_1$-$C_4$-alkanes are, in particular, carbon tetrachloride and chlorofluorocarbons such as 1,1,2,2-tetrachlorodifluoroethane and 1,1,2-trichlorotrifluoroethane.

Among partially halogenated $C_2$-$C_4$-alkenes, particular mention may be made of trichloroethylene, and among perhalogenated $C_2$-$C_4$-alkenes, particular mention may be made of tetrachloroethylene.

Five- and six-membered saturated cyclic ethers having one oxygen atom are, in particular, tetrahydrofuran and tetrahydropyran, and a six-membered saturated cyclic ether having two nonadjacent oxygen atoms which deserves particular mention is dioxane.

Among N,N-di($C_1$-$C_4$-alkyl)formamides and N,N-di($C_1$-$C_4$-alkyl)acetamides, particular mention may be made of dimethylformamide and dimethylacetamide.

Among five-, six- and seven-membered saturated lactones and lactams, particular mention may be made of γ-butyrolactone and N-methylpyrrolidinone.

$C_1$-$C_4$-Alkyl $C_1$-$C_4$-alkanoates are, in particular, methyl and ethyl formates and methyl, ethyl, propyl and butyl acetates.

In the process of the invention, particular preference is given to using a solvent or solvent mixture comprising one or more compounds selected from the group consisting of water, $C_1$-$C_4$-alkanols, in particular methanol, ethanol, propanol and isopropanol, symmetrical and unsymmetrical di($C_1$-$C_4$)-alkyl ketones, in particular acetone and methyl tert-butyl ketone, partially halogenated $C_1$-$C_4$-alkanes, in particular methylene chloride and chloroform, tetrahydrofuran, dioxane, N,N-dimethylformamide, N,N-dimethylacetamide, N-methylpyrrolidinone, $C_1$-$C_4$-alkyl formates, in particular methyl and ethyl formates, $C_1$-$C_4$-alkyl acetates, in particular methyl and ethyl acetates, dimethyl sulfoxide, butyl methyl sulfoxide, acetonitrile, propionitrile, benzonitrile, picolinonitrile, nicotinonitrile and isonicotinonitrile, benzene, toluene, o-, m- and p-xylene, pyridine and 2-, 3- and 4-methylpyridine.

In the process and its preferred embodiments, use is made of a Brönsted acid or a mixture of Brönsted acids which preferably comprises one or more compounds selected from the group consisting of hydrogen halides, water-free inorganic acids, water-free carboxylic acids, water-free aliphatic and aromatic sulfonic acids and water-free partially fluorinated and perfluorinated aliphatic and aromatic sulfonic acids.

Hydrogen halides are, for example, hydrogen chloride, hydrogen bromide and hydrogen iodide.

Water-free inorganic acids are, for example, sulfuric acid and phosphoric acid, and water-free carboxylic acids are, for example, formic acid, acetic acid and trifluoroacetic acid.

Among water-free aliphatic and aromatic sulfonic acids and water-free partially fluorinated and perfluorinated aliphatic and aromatic sulfonic acids, mention may be made of, for example, $H_3C$—$SO_3H$, $F_3C$—$SO_3H$, $F_3C$—$CH_2$—$SO_3H$, $F_9C_4$—$SO_3H$,

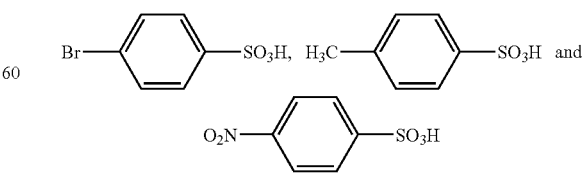

Particular preference is given to using a Brönsted acid or a mixture of Brönsted acids comprising one or more compounds selected from the group consisting of hydrogen chloride, hydrogen bromide, water-free sulfuric acid, water-free formic acid, water-free methanesulfonic acid, water-free trifluoromethanesulfonic acid, water-free trifluoroacetic acid and water-free acetic acid.

The one or more Brönsted acids can be used either as an aqueous solution together with one or more solvents other than water or as water-free compounds together with one or more solvents other than water.

In the process of the invention, it is advantageous for, firstly, the aqueous solution of the one or more Brönsted acids to be at least partially miscible with the solvent or solvent mixture and, secondly, for the compound $C^1$ or the mixture $M^1$ comprising the compound $C^1$ to dissolve at least partially either in the aqueous solution of the one or more Brönsted acids or the solvent or solvent mixture.

Furthermore, it is advantageous in the process of the invention if both the water-free Brönsted acid or the mixture of water-free Brönsted acids and the compound $C^1$ or the mixture $M^1$ comprising the compound $C^1$ is at least partially soluble in the solvent or solvent mixture.

For the purposes of the present invention, a solution of, for example, hydrogen chloride in ethanol comprising residual moisture is regarded as a solution of hydrogen chloride in a solvent mixture of water and ethanol.

The process of the invention and its preferred embodiments are preferably carried out using the Brönsted acid or the mixture of Brönsted acids in a total concentration of from $10^{-7}$ to 1 mol/l, preferably in a total concentration of from $10^{-5}$ to $10^{-1}$ mol/l, in the solvent or solvent mixture.

EXAMPLES

Example 1

Isomerization of mer-tris[N-(p-cyanophenyl)-N'-methylimidazolylidene-$C^2$,$C^{2'}$]iridium(III) to fac-tris[N-(p-cyanophenyl)-N'-methylimidazolylidene-$C^2$, $C^{2'}$]iridium(III)

A solution of pure mer-tris[N-(p-cyanophenyl)-N'-methylimidazolylidene-$C^2$,$C^{2'}$]-iridium(III) (20 mg, 27 μmol) in acetone (9.75 ml) was admixed at room temperature with 0.1 M hydrochloric acid (0.25 ml). The mixture was stirred under reflux for 4 hours. Subsequent removal of the volatile components on a rotary evaporator gave a yellowish solid which was dried under an oil pump vacuum. Yield: 20 mg (27 μmol, 100% of theory).

The molar ratio of fac to mer isomers was determined by $^1$H-NMR spectroscopy and found to be 3:1. Accordingly, the pure mer isomer was converted into a mixture which had a mole fraction of this isomer of 25% but had a mole fraction of 75% of the fac isomer.

The isomer mixture could be separated by column chromatography (silica gel, ethyl acetate/cyclohexane 9:1).

Yield: 15 mg of fac isomer (20 μmol, 75 mol %), 5 mg of mer isomer (7 μmol, 25 mol %).

Analysis of the Fac Isomer:
$^1$H-NMR ($d_6$-DMSO/$CD_2Cl_2$ 4:1, 500 MHz): δ=3.06 (s, 9H), 6.66 (d, J 2.0, 3H), 7.11 (d, J 2.0, 3H), 7.28 (dd, J 8.0, 2.0, 3H), 7.49 (d, J 8.0, 3H), 7.87 (d, J 2.0, 3H).

$^{13}$C-NMR ($d_6$-DMSO/$CD_2Cl_2$ 4:1, 500 MHz): δ=36.2, 107.0, 111.1, 115.5, 120.7, 122.4, 125.9, 139.7, 149.2, 151.5, 174.6.

ESI-MS (MeCN/$H_2O$ 8:2): m/z=737.1751 ($M^+$, correct isotope pattern, calc.: 737.1755), 755 ($M+NH_4^+$, correct isotope pattern).

The mer isomer which has been separated off can be subjected to a renewed isomerization according to the invention.

Example 2

Isomerization of tris[N,N'-diphenylbenzimidazolylidene-$C^2$,$C^{2'}$]iridium(III)

a) A sample of fac-tris[N,N'-diphenylbenzimidazolylidene-$C^2$,$C^{2'}$]iridium(III) was dissolved in chloroform comprising catalytic amounts of hydrogen chloride. The solution was heated at 40° C. overnight and subsequently freed of the solvent and hydrogen chloride under reduced pressure.

b) A sample of mer-tris[N,N'-diphenylbenzimidazolylidene-$C^2$,$C^{2'}$]iridium(III) was treated in the same way as under a).

It was established by means of NMR spectroscopy that the fac isomer was present unchanged in a), but the mer isomer had been converted completely into the fac isomer in b).

Analysis of the Fac Isomer:
$^1$H-NMR ($CD_2Cl_2$, 500 MHz):
δ=8.10 (d, 3H), 7.94 (d, 3H), 7.28 (m, 6H), 7.06 (m, 3H), 7.02 (m, 3H), 6.74 (m, 3H), 6.68 (m, 3H), 6.60 (d, 3H), 6.56 (d, 3H), 6.42 (d, 3H), 6.29 (m, 3H), 6.18 (d, 3H).

Analysis of the Mer Isomer:
$^1$H-NMR ($CD_2Cl_2$, 500 MHz, −20° C.):
δ=8.30 (d, 1H), 7.89 (m, 2H), 7.73 (d, 1H), 7.56 (d, 1H), 7.31 (d, 1H), 7.28-7.16 (m, 5H), 7.08-7.01 (m, 3H), 6.98 (m, 1H), 6.93 (m, 1H), 6.85-6.20 (m, 21H), 5.78 (d, 1H), 5.64(d, 1H).

The invention claimed is:
1. A process for converting a compound $C^1$ of the formula I in a mer isomer form

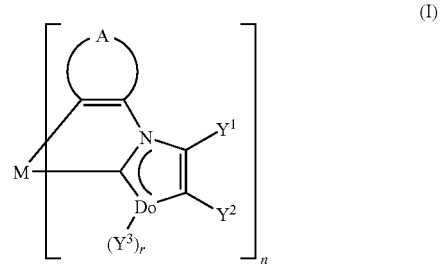

into an isomeric compound $C^2$ of the formula I in a fac isomer form, where the variables have the following meanings:

n is 2 or 3;

M is Pd or Pt, in each case in the formal oxidation state +II, when n is 2;

and is Ru, Os, Co, Rh or Ir, in each case in the formal oxidation state +III, when n is 3;

Do is a donor atom selected from the group consisting of N and P;

r is 1 when Do is N or P;

$Y^1$, $Y^2$ are each, independently of one another, hydrogen, alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ or NO, or $Y^1$ and $Y^2$ together with the carbon atoms to which they are bound form a six-membered aromatic ring which may comprise one or two nitrogen atoms and may optionally be fused with a further, optionally fused and optionally heteroatom-comprising ring;

$Y^3$ is alkyl, alkenyl, alkynyl, aryl or heteroaryl;

A is a bridge having three or four atoms of which one or two atoms may be heteroatoms and the remaining atoms are carbon atoms, so that the group

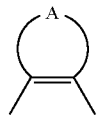

forms a five- or six-membered heteroaromatic ring or benzene ring which may optionally be substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO and may optionally be fused with a further, optionally heteroatom-comprising ring which may likewise be fused and substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO;

which comprises allowing a Brönsted acid or a mixture of Brönsted acids to act on $C^1$ in the presence of a solvent or solvent mixture at a temperature of from 0° C. to the boiling point of the solvent or the solvent mixture, with the proviso that a) the formation of $C^2$ from $C^1$ occurs under the conditions of the process and b) when both $C^1$ and $C^2$ are present as a mixture prior to the Brönsted acid acting on $C^1$, the respective isomer ratios of $C^1$ and $C^2$ are different before and after the Brönsted acid acts on $C^1$.

2. The process according to claim 1, wherein the variables in formula I have the following meanings:

n is 2 or 3;

M is Pd or Pt, in each case in the formal oxidation state +II, when n is 2;

and is Rh or Ir, in each case in the formal oxidation state +III, when n is 3;

Do is a donor atom N;

r is 1;

$Y^1, Y^2$ are each, independently of one another, hydrogen or alkyl or $Y^1$ and $Y^2$ together with the carbon atoms to which they are bound form a six-membered aromatic ring which may comprise one or two nitrogen atoms;

$Y^3$ is alkyl, aryl or heteroaryl;

A is a bridge having three or four atoms of which one or two atoms may be heteroatoms and the remaining atoms are carbon atoms, so that the group

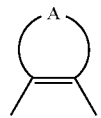

forms a five- or six-membered heteroaromatic ring or benzene ring which may optionally be substituted by substituents selected from the group consisting of alkyl, alkenyl, alkynyl, aryl, heteroaryl, alkyloxy, aryloxy, alkylthio, arylthio, alkylcarbonyl, arylcarbonyl, carboxyl, alkyloxycarbonyl, aryloxycarbonyl, hydroxysulfonyl, alkyloxysulfonyl, aryloxysulfonyl, halogen, CN, CHO, $NO_2$ and NO.

3. The process according to claim 1, wherein the variables in formula I have the following meanings:

n is 2 or 3;

M is Pd or Pt, in each case in the formal oxidation state +II, when n is 2;

and is Rh or Ir, in each case in the formal oxidation state +III, when n is 3;

Do is a donor atom N;

r is 1;

$Y^1, Y^2$ are each, independently of one another, hydrogen or alkyl or $Y^1$ and $Y^2$ together with the carbon atoms to which they are bound form a benzene ring;

$Y^3$ is alkyl or aryl;

A is a bridge having four atoms of which one atom may be a heteroatom and the remaining atoms are carbon atoms, so that the group

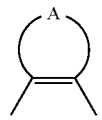

forms a six-membered heteroaromatic ring or benzene ring which may optionally be substituted by substituents selected from the group consisting of alkyl, alkyloxy, aryl, aryloxy, alkylcarbonyl, arylcarbonyl, alkoxycarbonyl, aryloxycarbonyl, halogen and CN.

4. The process according to claim 1, wherein the variables in formula I have the following meanings:

n is 2 or 3;

M is Pd or Pt, in each case in the formal oxidation state +II, when n is 2;

and is Rh or Ir, in each case in the formal oxidation state +III, when n is 3;

Do is a donor atom N;

r is 1;

$Y^1, Y^2$ are each hydrogen or $Y^1$ and $Y^2$ together with the carbon atoms to which they are bound form a benzene ring;

$Y^3$ is alkyl or aryl;

A is a bridge having four atoms of which one atom may be a nitrogen atom and the remaining atoms are carbon atoms, so that the group

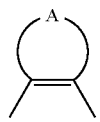

forms a pyridine or benzene ring which may optionally be substituted by substituents selected from the group consisting of alkyl, alkyloxy, aryl, aryloxy, alkylcarbonyl, arylcarbonyl, alkoxycarbonyl, aryloxycarbonyl, halogen and CN.

5. The process according to claim 1, wherein the solvent or solvent mixture comprises one or more compounds selected from the group consisting of water, $C_1$-$C_4$-alkanols, symmetrical and unsymmetrical di($C_1$-$C_4$)-alkyl ethers, symmetrical and unsymmetrical di($C_1$-$C_4$)-alkyl ketones, partially halogenated $C_1$-$C_4$-alkanes, perhalogenated $C_1$-$C_4$-alkanes, partially halogenated $C_2$-$C_4$-alkenes, perhalogenated $C_2$-$C_4$-alkenes, five- and six-membered saturated cyclic ethers having one oxygen atom, six-membered saturated cyclic ethers having two nonadjacent oxygen atoms, N—$C_1$-$C_4$-alkylformamides, N,N-di($C_1$-$C_4$-alkyl)formamides, N—$C_1$-$C_4$-alkylacetamides, N,N-di($C_1$-$C_4$-alkyl)acetamides, five-, six- and seven-membered saturated lactones, five-, six- and seven-membered saturated lactams, $C_1$-$C_4$-alkyl $C_1$-$C_4$-alkanoates, symmetrical and unsymmetrical di($C_1$-$C_4$)-alkyl sulfoxides, nitriles of $C_2$-$C_4$-carboxylic acids, nitriles of monocyclic aromatic carboxylic acids, monocyclic aromatics and monocyclic heteroaromatics.

6. The process according to claim 1, wherein the solvent or solvent mixture comprises one or more compounds selected from the group consisting of water, $C_1$-$C_4$-alkanols, symmetrical and unsymmetrical di($C_1$-$C_4$)-alkyl ketones, partially halogenated $C_1$-$C_4$-alkanes, tetrahydrofuran, dioxane, N,N-dimethylformamide, N,N-dimethylacetamide, γ-butyrolactone, N-methylpyrrolidinone, $C_1$-$C_4$-alkyl formates, $C_1$-$C_4$-alkyl acetates, dimethyl sulfoxide, butyl methyl sulfoxide, acetonitrile, propionitrile, benzonitrile, picolinonitrile, nicotinonitrile and isonicotinonitrile, benzene, toluene, o-, m- and p-xylene, pyridine and 2-, 3- and 4-methylpyridine.

7. The process according to claim 1, wherein the Brönsted acid or the mixture of Brönsted acids comprises one or more compounds selected from the group consisting of hydrogen halides, water-free inorganic acids, water-free carboxylic acids, water-free aliphatic and aromatic sulfonic acids and water-free partially fluorinated and perfluorinated aliphatic and aromatic sulfonic acids.

8. The process according to claim 1, wherein the Brönsted acid or the mixture of Brönsted acids comprises one or more compounds selected from the group consisting of hydrogen chloride, hydrogen bromide, water-free sulfuric acid, water-free formic acid, water-free methanesulfonic acid, water-free trifluoromethanesulfonic acid, water-free trifluoroacetic acid and water-free acetic acid.

9. The process according to claim 1, wherein the Brönsted acid or the mixture of Brönsted acids is used in a total concentration of from $10^{-7}$ to 1 mol/l, in the solvent or solvent mixture.

10. The process according to claim 1, wherein the Brönsted acid or the mixture of Brönsted acids is used in a total concentration of from $10^{-5}$ to $10^{-1}$ mol/l, in the solvent or solvent mixture.

11. The process according to claim 1, wherein M is Pd or Pt and Do is N.

12. The process according to claim 1, wherein M is Ir and the compound $C^1$ is at least one of mer-tris[N-(p-cyanophenyl)-M-methylimidazolylidene-$C^2$,$C^{2'}$]—Ir(III) and tris[N,N'-diphenylbenzimidazolylidene-$C^2$,$C^{2'}$]Ir(III).

13. The process according to claim 1, wherein the Brönsted acid comprises hydrochloric acid.

* * * * *